United States Patent
Ghosh et al.

[11] Patent Number: 6,153,633
[45] Date of Patent: Nov. 28, 2000

[54] STABLE 3-ISOTHIAZOLONE COMPOSITIONS

[75] Inventors: Tirthankar Ghosh, Oreland; David Willard Potter, North Wales, both of Pa.

[73] Assignee: Rohm and Haas Company, Philadelphia, Pa.

[21] Appl. No.: 09/334,440

[22] Filed: Jun. 16, 1999

Related U.S. Application Data

[60] Provisional application No. 60/096,052, Aug. 18, 1998.

[51] Int. Cl.[7] .......................... A61K 31/425; A61K 31/15
[52] U.S. Cl. ............................................. 514/372; 514/664
[58] Field of Search ...................... 514/372, 664

[56] References Cited

U.S. PATENT DOCUMENTS

| | | | |
|---|---|---|---|
| 5,160,526 | 11/1992 | Ghosh et al. | 71/67 |
| 5,725,806 | 3/1998 | Ghosh | 252/405 |
| 5,756,005 | 5/1998 | Ghosh et al. | 252/405 |

FOREIGN PATENT DOCUMENTS

4411750 B1  5/1994  European Pat. Off. .

OTHER PUBLICATIONS

"Synthesis And Antimicrobial Activity Of Diacylhydrazines and Analogs", by Ruben H. Edrosa and Susana M. Sicardi; Acta Farm. Bonaerense 3(1): 15–19 (1984).

"Substituted Diazenes: Effect on the Growth of Enterobacteria and Possible Use as Selective Agents for Isolation of Pseudomonads", by Michael J. Rose, Nancy K. Enkiri, and William L. Sulzbacher; Applied Microbiology, Dec. 1971, pp. 1141–1146.

*Primary Examiner*—Kevin E. Weddington
*Attorney, Agent, or Firm*—Joanne P. Will; S. Matthew Cairns

[57] ABSTRACT

Disclosed are stable microbicidal compositions of 3-isothiazolone compounds and azobiscarbonyl compounds. Also disclosed are methods of stabilizing 3-isothiazolone compounds against chemical decomposition by combining with the 3-isothiazolones a stabilizing amount of an azobiscarbonyl compound.

9 Claims, No Drawings

STABLE 3-ISOTHIAZOLONE COMPOSITIONS

This application claims benefit to provisional application 60/096,052 filed Aug. 18, 1998.

BACKGROUND OF THE INVENTION

This invention relates to the stabilization of microbicides. In particular, this invention relates to the improved stabilization of 3-isothiazolone microbicides.

Microbicides are used commercially to prevent the growth of microbes in a variety of loci, such as cooling towers, metal working fluid systems, paint and cosmetics. One of the more important classes of microbicides is 3-isothiazolones. Many 3-isothiazolones have achieved commercial success because they are very effective in preventing microbial growth under a wide variety of conditions and in a variety of loci. Among the most important 3-isothiazolones are 5-chloro-2-methyl-3-isothiazolone, 2-methyl-3-isothiazolone, 2-n-octyl-3-isothiazolone, 4,5-dichloro-2-n-octyl-3-isothiazolone and mixtures thereof.

Typical 3-isothiazolone products of a 3:1 mixture of 5-chloro-2-methyl-3-isothiazolone and 2-methyl-3-isothiazolone contain between 0.5 and 35 percent by weight of the 3-isothiazolone mixture and a similar amount of a stabilizer. Concentrate compositions of a 3:1 mixture of 5-chloro-2-methyl-3-isothiazolone and 2-methyl-3-isothiazolone generally contain about 5 to 35 percent by weight of the 3-isothiazolone compounds and require about 10 to 25 percent by weight of a stabilizer. Dilute solutions of a 3:1 mixture of 5-chloro-2-methyl-3-isothiazolone and 2-methyl-3-isothiazolone contain about 0.5 to 5 percent by weight of the 3-isothiazolone compounds. These dilute solutions typically contain from 1 to 25 percent by weight of a stabilizer for the 3-isothiazolones.

While 3-isothiazolones are very effective microbicides, they suffer from being unstable under certain conditions. Without the presence of a stabilizer, many 3-isothiazolones chemically degrade and lose microbicidal efficacy, especially in aqueous systems. Much research has been devoted to stabilizing 3-isothiazolones.

Many of the methods developed to stabilize 3-isothiazolone compounds use inorganic salts. For example, the most commercially successful stabilizers for 3-isothiazolone compounds are metal nitrate salts. To be effective in stabilizing 3-isothiazolone compounds, high levels (for example 14% wt) of metal nitrate salts are typically required. The presence of these high salt levels can cause coagulation of latexes.

Some organic stabilizers have been developed for 3-isothiazolone compounds. For example, EP 411 750 A (Mattox) discloses the use of various organic compounds as stabilizers for 3-isothiazolones. Such organic compounds include dialkyl- and dicycloalkyl-carbodiimides. The problem with these organic compounds is that they work only in non-aqueous systems.

There is thus a continuing need for stabilizers for 3-isothiazolones that can be used in both aqueous and non-aqueous systems and do not cause coagulation of latexes.

SUMMARY OF THE INVENTION

The present invention is directed to stable microbicidal compositions comprising one or more 3-isothiazolone compounds and a stabilizing amount of an azobiscarbonyl compound of the formula

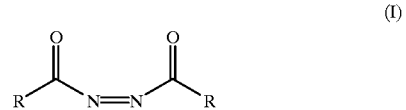

wherein R=NR$^1$R$^2$, OR$^3$, R$^4$; R$^1$, R$^2$, R$^3$, R$^4$=H, (C$_1$–C$_{12}$) alkyl, substituted (C$_1$–C$_{12}$)alkyl, (C$_2$–C$_{12}$)alkenyl, substituted (C$_2$–C$_{12}$) alkenyl, (C$_2$–C$_{12}$)alkynyl, substituted (C$_2$–C$_{12}$)alkynyl, (C$_7$–C$_{10}$)aralkyl, substituted (C$_7$–C$_{10}$) aralkyl, aryl, substituted aryl; and R$^1$ and R$^2$ may be joined together to form a 5–7 membered ring.

The present invention is also directed to a method of stabilizing one or more 3-isothiazolone compounds comprising combining with the 3-isothiazolone compound a stabilizing amount of an azobiscarbonyl compound as described above.

The present invention is further directed to a method of controlling or inhibiting the growth of microorganisms in a locus comprising introducing to the locus a composition as described above.

DETAILED DESCRIPTION OF THE INVENTION

As used throughout the specification, the following terms shall have the following meanings, unless the context clearly indicates otherwise.

The term "microbicide" refers to a compound capable of inhibiting the growth of or controlling the growth of microorganisms at a locus. The term "microorganism" includes, but is not limited to, fungi, bacteria, and algae. The term "locus" refers to an industrial system or product subject to contamination by microorganisms. "Carrier" refers to any material that can be used to dissolve, disperse or dispense the composition incorporated therewith without impairing the microbicidal effectiveness of the 3-isothiazolone compound.

"Alkyl," "alkenyl" and "alkynyl" refer to straight chain, branched, or cyclic carbon chains, or any combination thereof. "Substituted alkyl," "substituted alkenyl" and "substituted alkynyl" mean one or more of the hydrogens on the carbon chain are replaced by another substituent, such as cyano, hydroxy, (C$_1$–C$_4$)alkyl, nitro, mercapto, (C$_1$–C$_4$) alkylthio, halo and (C$_1$–C$_4$)alkoxy. "Halo" and "halogen" refer to fluorine, chlorine, bromine and iodine. "Substituted aralkyl" means one or more hydrogens on the aromatic ring or alkyl chain are replaced by another substituent, such as cyano, hydroxy, (C$_1$–C$_4$)alkyl, nitro, mercapto, (C$_1$–C$_4$) alkylthio, halo and (C$_1$–C$_4$)alkoxy. "Aryl" refers to phenyl, fused aromatic rings, heteroaromatic rings and fused heteroaromatic rings. "Substituted aryl" means one or more of the hydrogens on the aryl ring are replaced by another substituent, such as cyano, hydroxy, (C$_1$–C$_4$)alkyl, nitro, mercapto, (C$_1$–C$_4$)alkylthio, halo and (C$_1$–C$_4$)alkoxy. "Heteroaromatic" refers to a 5–7 membered aromatic ring having one or more heteroatoms in the ring.

All amounts are percent by weight ("%wt"), unless otherwise noted. All ranges are inclusive. As used throughout the specification, the following abbreviations are applied: g=gram; C=Centigrade; HPLC=high performance liquid chromatography; DI=deionized; MW=molecular weight; and ppm=parts per million.

Any 3-isothiazolone compound is useful in the compositions of the present invention. Suitable 3-isothiazolone compounds include, but are not limited to: 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; 2-n-octyl-3-isothiazolone; 4,5-dichloro-2-n-octyl-3-isothiazolone; 1,2-benzisothiazolone; 4,5-trimethylene-2-methyl-3-isothiazolone; and mixtures thereof. When mixtures of 5-chloro-2-methyl-3-isothiazolone and 2-methyl-3-isothiazolone are used, the weight ratio of 5-chloro-2-methyl-3-isothiazolone to 2-methyl-3-isothiazolone is generally 99:1 to 1:99, preferably 90:10 to 70:30.

In general, the amount of 3-isothiazolone compound useful in the compositions of the present invention is 0.5 to 35% wt, based on the weight of the composition, and preferably 1 to 25% wt.

The azobiscarbonyl compounds useful as stabilizers for 3-isothiazolone compounds are those of formula (I), above. It is preferred that $R^1$, $R^2$, $R^3$ and $R^4$ are hydrogen, ($C_1$–$C_{12}$) alkyl and substituted ($C_1$–$C_{12}$)alkyl, and more preferably ($C_1$–$C_8$)alkyl and substituted ($C_1$–$C_8$)alkyl. When $R^1$, $R^2$, $R^3$ or $R^4$ is alkynyl, it is preferred that the alkynyl is propynyl or halopropynyl.

Preferred azobiscarbonyl compounds are those wherein $R=NR^1R^2$. When $R^1$ and $R^2$ are joined to form a 5–7 membered ring, such ring may be saturated or unsaturated. These 5–7 membered rings may contain one or more additional heteroatoms, such as sulfur and oxygen. Suitable 5–7 membered rings include, but are not limited to: piperidine, morpholine, and pyrrolidine.

When the aryl group is a heteroaromatic ring, it is preferred that the heteroaromatic ring have one or more heteroatoms selected from nitrogen, oxygen and sulfur. Suitable heteroaromatic rings include, but are not limited to: thiophene, pyridine and furan.

Suitable fused aromatic rings useful as aryl groups in the present invention include, but are not limited to: naphthalene, indene and substituted naphthalene, such as naphthalene dicarboxylates. Suitable fused heteroaromatic rings include, but are not limited to: benzothiophene, benzothiazole, and indazole.

Suitable azobiscarbonyl compounds useful in the present invention include, but are not limited to: 1,1'-azobis(N,N-dimethylformamide); azodicarbonamide; N,N'-dicyclohexyl-diazenedicarboxamide; N,N'-bis(2-methoxyethyl)diazenedicarboxamide; N-ethyl-N'-phenyl-diazenecarboxamide; N,N'-dibutyl-diazenedicarboxamide; N,N'-bis-(1-methylpropyl)-diazenedicarboxamide; N-butyl-N'-cyclohexyl-diazenedicarboxamide; N-butyl-N'-(1-methylethyl)-diazenedicarboxamide; N,N'-dihexyl-diazenecarboxamide; N,N'-bis-(3-methylbutyl)-diazenecarboxamide; N,N'-didodecyl-diazenecarboxamide; N,N'-bis(phenylmethyl)-diazenecarboxamide; bis-(1-oxotetradecyl)-diazene; bis-(1-oxodecyl)-diazene; bis-(1-oxododecyl)-diazene; diethyl diazenedicarboxalate; dimethyl diazenedicarboxalate; bis-(1,1-dimethylethyl) diazenedicarboxalate; bis-(phenylmethyl) diazenedicarboxalate; and 1,1'-(azodicarbonyl)dipiperidine. Preferred azobiscarbonyl compounds are 1,1'-azobis(N,N-dimethylformamide) and azodicarbonamide.

Any amount of azobiscarbonyl compound sufficient to stabilize the 3-isothiazolone compound is suitable for use in the present invention. In general, the amount of azobiscarbonyl compound sufficient to stabilize the 3-isothiazolone compound is 0.01 to 15% wt, based on the weight of the composition. It is preferred that the amount of azobiscarbonyl compound is 0.1 to 10% wt, and more preferably 0.5 to 8% wt. The specific amount of azobiscarbonyl compound will depend upon the particular azobiscarbonyl compound and the amount of the 3-isothiazolone compound in the composition. More azobiscarbonyl compound is needed when more 3-isothiazolone compound is present. For example, 0.1 to 2 % wt of azobiscarbonyl compound is typically sufficient to stabilize 1.5% wt of 3-isothiazolone compound while 6 to 10% wt of azobiscarbonyl compound is typically sufficient to stabilize 14% wt of 3-isothiazolone compound. The azobiscarbonyl compounds useful in the present invention are generally commercially available, for example, from Aldrich Chemical Company (Milwaukee, Wis.) and may be used without further purification.

The compositions of the present invention may optionally contain a carrier. The carriers may be either solids or liquids. Suitable solid carriers include, but are not limited to: silicas, diatomaceous earth, inorganic salts and cyclodextrins. Liquid carriers include water, organic solvents and mixtures thereof. Suitable liquid carriers include, but are not limited to: water, methanol, ethanol, benzyl alcohol, ethylene glycol, diethylene glycol, polyethylene glycol, propylene glycol, dipropylene glycol, polypropylene glycol, phenoxyethanol, phenoxypropanol, xylene, toluene, methyl isobutyl ketone, methyl isoamyl ketone, and mixtures thereof.

When the compositions of the present invention contain a solid carrier, they may be added directly to the locus to be protected or may be formed into bricks, tablets, briquettes, blocks, pucks, prills and the like, and then added to the locus to be protected. When the compositions of the present invention contain a liquid carrier, they are typically added directly to the locus to be protected.

When a liquid carrier is used in the present invention, the amount of the azobiscarbonyl compound that may be used is not limited to the amount that is soluble in the carrier. Thus, an amount of the azobiscarbonyl compound above its solubility limit in the carrier may be used. When an azobiscarbonyl compound is used in excess of its solubility limit in the liquid carrier, the excess compound may be added to the composition in any way that will allow for more of the azobiscarbonyl compound to dissolve as needed. For example, the excess azobiscarbonyl compound may be added to the composition in a liquid permeable bag. Thus, a solution of a 3:1 mixture of 5-chloro-2-methyl-3-isothiazolone and 2-methyl-3-isothiazolone in water can be stabilized by the slightly water-soluble compound azodicarbonamide by adding the azocarbonamide to the solution in a water-permeable bag.

The compositions of the present invention may be prepared by combining the 3-isothiazolone compounds with the azobiscarbonyl compounds in any order. It is preferred that the azobiscarbonyl compound be added to the 3-isothiazolone compound. When a liquid carrier is used, it is preferred that the 3-isothiazolone compound is combined with the liquid carrier before the azobiscarbonyl compound is added.

The stability of the 3-isothiazolone compounds may be improved under certain conditions by the addition of one or more other stabilizers. Thus, other known 3-isothiazolone stabilizers may be combined advantageously with the stabilizers of the present invention. Any known 3-isothiazolone stabilizer is suitable for use in combination with the stabilizers of the present invention as long as it does not destabilize, or otherwise react with, the azobiscarbonyl stabilizers of the present invention. Other stabilizers suitable for use in combination with the azobiscarbonyl stabilizers of the present invention include, but are not limited to: alkyl disulfides, aromatic disulfides, trialkyl orthoformates, pyridine, pyridine N-oxide, metal nitrate salts, iodic acid, iodic acid salts, periodic acid, periodic acid salts, copper salts, and the like.

The compositions of the present invention can be used to inhibit the growth of microorganisms by introducing a microbicidally effective amount of the compositions onto, into, or at a locus subject to microbial attack. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas. Preferred loci are cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

The amount of 3-isothiazolone compounds suitable to inhibit or control the growth of microorganisms is well known in the art and depends upon the locus to be protected. The amount of 3-isothiazolone microbicide suitable to inhibit the growth of microorganisms is generally between 0.05 and 5,000 ppm, based on the volume of said locus to be protected. It is preferred to use between 0.1 and 2,500 ppm. For example, loci such as a cooling towers or pulp and paper processing fluids require 0.1 to 100 ppm of the 3-isothiazolone microbicides to inhibit microorganism growth. Other loci, such as construction products, oilfield fluids or emulsions, require 0.5 to 5000 ppm of the 3-isothiazolone microbicides to inhibit microorganism growth, while loci such as disinfectants or sanitizers may require up to 5,000 ppm.

It is known in the art that the performance of antimicrobial agents may be enhanced by combination with one or more other antimicrobial agents. Thus, other known microbicidal agents may be combined advantageously with the compositions of the present invention.

The following examples are presented to illustrate further various aspects of the present invention, but are not intended to limit the scope of the invention in any aspect. In the following examples, samples were considered stable when at least 50 percent of the 3-isothiazolones remained after 1 week of storage at 55° C.

EXAMPLE 1

Five samples of a solution of a 3:1 mixture of 5-chloro-2-methyl-3-isothiazolone ("CMI") and 2-methyl-3-isothiazolone ("MI") in DI water were prepared. One sample served as Control and the other samples were labeled A-D. The Control contained only the 3-isothiazolone mixture and DI water. Samples A-D contained the 3-isothiazolone mixture, DI water and 1,1'-azobis(N,N-dimethylformamide) as stabilizer. In addition, Sample B contained 2,2'-dithiobis (pyridine-N-oxide) as a second stabilizer. The amounts of the 3-isothiazolone and stabilizers in the Control and Samples A-D are reported in Table 1. The remainder of each sample was DI water.

An aliquot was removed from each sample for initial analysis. The samples were then placed in a 55° C. oven. Aliquots were removed after 2 and 4 weeks storage and analyzed by HPLC for the total amount of 3-isothiazolone remaining. The results are reported in Table 1. Stabilizer A is 1,1'-azobis(N,N-dimethylformamide) and Stabilizer B is 2,2'-dithiobis(pyridine-N-oxide).

TABLE 1

Percent of 3-Isothiazolone Remaining After Storage

| Sample | CMI + MI Initial % wt | Stabilizer A (% wt) | Stabilizer B (% wt) | 2 Weeks | 4 Weeks |
|---|---|---|---|---|---|
| Control | 1.5 | 0 | 0 | 0 | 0 |
| A | 1.5 | 0.9 | 0 | 100 | 100 |
| B | 1.5 | 0.9 | 0.3 | 100 | 89 |
| C | 4.7 | 3.0 | 0 | 100 | 100 |
| D | 1.4 | 0.9 | 0 | 100 | 100 |

The above data clearly show that the azobiscarbonyl compounds of the present invention are effective at stabilizing 3-isothiazolone compounds.

EXAMPLE 2

Six samples of a solution of a 3:1 mixture of CMI and MI in DI water were prepared. Two samples served as Controls and the other samples were labeled E-H. The Controls contained only the 3-isothiazolone mixture and DI water. Samples E-H contained the 3-isothiazolone mixture, DI water and azodicarbonamide as stabilizer. The amounts of the 3-isothiazolone and stabilizer in the Controls and Samples E-H are reported in Table 2. The remainder of each sample was DI water.

Due to its limited water solubility, the azodicarbonamide was placed in water-permeable bags having a MW cut off of 3500. One bag was then placed in each of Samples E-H. An aliquot was then removed from each sample for initial analysis. The samples were then placed in a 55° C. oven. Aliquots were removed after 1, 2 and 4 weeks storage and analyzed by HPLC for the total amount of 3-isothiazolone remaining. The results are reported in Table 2.

TABLE 2

Percent of 3-Isothiazolones Remaining After Storage

| Sample | CMI + MI Initial % wt | Stabilizer (% wt) | 1 Week | 2 Weeks | 4 Weeks |
|---|---|---|---|---|---|
| Control | 5.6 | 0 | 19 | 3 | 0 |
| Control | 14.0 | 0 | 43 | 3 | 0 |
| E | 5.6 | 3.3 | 98 | 97 | 100 |
| F | 12.2 | 6.0 | 98 | 92 | 40 |
| G | 5.6 | 3.3 | 100 | 100 | 99 |
| H | 16.0 | 5.5 | 54 | 15 | 0 |

The above data clearly show that azobiscarbonyl compounds of the present invention stabilize 3-isothiazolone compounds even when only slightly soluble in the liquid carrier.

EXAMPLE 3

One sample, labeled I, of a solution of 0.27 g of a 3:1 mixture of CMI and MI in 14.6 g of DI water was prepared. To this solution was added 0.2 g of 1,1'-(azodicarbonyl) dipiperidine as a stabilizer. The sample was mixed, but not all of the stabilizer dissolved. The undissolved stabilizer remained at the bottom of the sample jar. This sample was compared to a Control sample containing only a 3:1 mixture of CMI and MI in DI water. The amounts of the 3-isothiazolone and stabilizer in the sample and the Control are reported in Table 3.

An aliquot was removed from the sample for initial analysis. The sample was then placed in a 55° C. oven. An aliquots was removed after 1 week of storage and analyzed by HPLC for the total amount of 3-isothiazolone remaining. The results are reported in Table 3.

TABLE 3

| | Percent of 3-Isothiazolone Remaining | | |
|---|---|---|---|
| Sample | CMI + MI Initial % wt | Stabilizer (% wt) | 1 Week |
| Control | 5.6 | 0 | 19 |
| I | 1.5 | 1.3 | 78 |

These data show that the azobiscarbonyl compounds of the present invention stabilize 3-isothiazolone compounds even when only slightly soluble in the liquid carrier.

What is claimed is:

1. A stable microbicidal composition comprising one or more 3-isothiazolone compounds and a stabilizing amount of an azobiscarbonyl compound of the formula

wherein:

R=NR$^1$R$^2$, OR$^3$, R$^4$;

R$^1$, R$^2$, R$^3$, R$^4$=H, (C$_1$–C$_{12}$)alkyl, substituted (C$_1$–C$_{12}$) alkyl, (C$_2$–C$_{12}$)alkenyl, substituted (C$_2$–C$_{12}$)alkenyl, (C$_2$–C$_{12}$)alkynyl, substituted (C$_2$–C$_{12}$)alkynyl, (C$_7$–C$_{10}$)aralkyl, substituted (C$_7$–C$_{10}$)aralkyl, aryl, substituted aryl; and R$^1$ and R$^2$ may be joined together to form a 5–7 membered ring.

2. The composition of claim 1 wherein the 3-isothiazolone compound is selected from the group consisting of 5-chloro-2-methyl-3-isothiazolone; 2-methyl-3-isothiazolone; 2-ethyl-3-isothiazolone; 5-chloro-2-ethyl-3-isothiazolone; 4,5-dichloro-2-methyl-3-isothiazolone; 2-n-octyl-3-isothiazolone; 4,5-dichloro-2-n-octyl-3-isothiazolone; 1,2-benzisothiazolone; 4,5-trimethylene-2-methyl-3-isothiazolone; and mixtures thereof.

3. The composition of claim 1 wherein the amount of 3-isothiazolone compound is 0.5 to 35 wt %, based on the weight of the composition.

4. The composition of claim 1 wherein R is NR$^1$R$^2$.

5. The composition of claim 4 wherein R$^1$ and R$^2$ are independently selected from H and (C$_1$–C$_{12}$)alkyl.

6. The composition of claim 1 wherein the azobiscarbonyl is selected from the group consisting of: 1,1'-azobis(N,N-dimethylformamide); azodicarbonamide; N,N'-dicyclohexyl-diazenedicarboxamide; N,N'-bis(2-methoxyethyl)diazenedicarboxamide; N-ethyl-N'-phenyl-diazenecarboxamide; N,N'-dibutyl-diazenedicarboxamide; N,N'-bis-(1-methylpropyl)-diazenedicarboxamide; N-butyl-N'-cyclohexyl-diazenedicarboxamide; N-butyl-N'-(1-methylethyl)-diazenedicarboxamide; N,N'-dihexyl-diazenecarboxamide; N,N'-bis-(3-methylbutyl)-diazenecarboxamide; N,N'-didodecyl-diazenecarboxamide; N,N'-bis(phenylmethyl)-diazenecarboxamide; bis-(1-oxotetradecyl)-diazene; bis-(1-oxodecyl)-diazene; bis-(1-oxododecyl)-diazene; diethyl diazenedicarboxalate; dimethyl diazenedicarboxalate; bis-(1,1-dimethylethyl) diazenedicarboxalate; bis-(phenylmethyl) diazenedicarboxalate; and 1,1'-(azodicarbonyl)dipiperidine.

7. The composition of claim 1 wherein the azobiscarbonyl compound is 0.01 to 15% wt, based on the composition.

8. A method of stabilizing one or more 3-isothiazolone compounds comprising combining with the 3-isothiazolone compound a stabilizing amount of an azobiscarbonyl compound of the formula

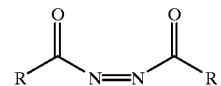

wherein:

R=NR$^1$R$^2$, OR$^3$, R$^4$;

R$^1$, R$^2$, R$^3$, R$^4$=H, (C$_1$–C$_{12}$)alkyl, substituted (C$_1$–C$_{12}$) alkyl, (C$_2$–C$_{12}$)alkenyl, substituted (C$_2$–C$_{12}$)alkenyl, (C$_2$–C$_{12}$)alkynyl, substituted (C$_2$–C$_{12}$)alkynyl, (C$_7$–C$_{10}$)aralkyl, substituted (C$_7$–C$_{10}$)aralkyl, aryl, substituted aryl; and R$^1$ and R$^2$ may be joined together to form a 5–7 membered ring.

9. The method of claim 8 wherein the azobiscarbonyl compound is selected from the group consisting of: 1,1'-azobis(N,N-dimethylformamide); azodicarbonamide; N,N'-dicyclohexyl-diazenedicarboxamide; N,N'-bis(2-methoxyethyl)diazenedicarboxamide; N-ethyl-N'-phenyl-diazenecarboxamide; N,N'-dibutyl-diazenedicarboxamide; N,N'-bis-(1-methylpropyl)-diazenedicarboxamide; N-butyl-N'-cyclohexyl-diazenedicarboxamide; N-butyl-N'-(1-methylethyl)-diazenedicarboxamide; N,N'-dihexyl-diazenecarboxamide; N,N'-bis-(3-methylbutyl)-diazenecarboxamide; N,N'-didodecyl-diazenecarboxamide; N,N'-bis(phenylmethyl)-diazenecarboxamide; bis-(1-oxotetradecyl)-diazene; bis-(1-oxodecyl)-diazene; bis-(1-oxododecyl)-diazene; diethyl diazenedicarboxalate; dimethyl diazenedicarboxalate; bis-(1,1-dimethylethyl) diazenedicarboxalate; bis-(phenylmethyl) diazenedicarboxalate; and 1,1'-(azodicarbonyl)dipiperidine.

* * * * *